United States Patent
Sameshima et al.

(10) Patent No.: US 6,270,789 B1
(45) Date of Patent: Aug. 7, 2001

(54) BASE FOR SUPPOSITORY

(75) Inventors: Teruyuki Sameshima, Ayabe; Kengo Omachi; Izumi Fukuda, both of Fukuchiyama, all of (JP)

(73) Assignee: Amato Pharmaceutical Products, Ltd., Kyoto (JP)

( * ) Notice: Subject to any disclaimer, the term of this patent is extended or adjusted under 35 U.S.C. 154(b) by 0 days.

(21) Appl. No.: 09/487,248

(22) Filed: Jan. 19, 2000

(30) Foreign Application Priority Data

Jan. 29, 1999 (JP) .................................................. 11-023101
Oct. 14, 1999 (JP) .................................................. 11-292857

(51) Int. Cl.$^7$ ................................. A61F 13/00; A61F 6/06
(52) U.S. Cl. .......................... 424/433; 424/430; 424/436; 424/422; 514/966; 514/967; 514/968
(58) Field of Search ..................................... 424/434, 430, 424/433, 422, 80, 436; 514/2, 397, 967, 966, 968

(56) References Cited

U.S. PATENT DOCUMENTS

| | | | |
|---|---|---|---|
| 4,765,978 | 8/1988 | Abidi et al. | 424/80 |
| 4,871,777 | * 10/1989 | Breitzke | 514/785 |
| 5,783,555 | * 7/1998 | Suzuki et al. | 514/2 |

FOREIGN PATENT DOCUMENTS

55081812 * 6/1980 (JP) .
63179820 * 7/1988 (JP) .

* cited by examiner

Primary Examiner—Thurman K. Page
Assistant Examiner—Blessing Fubara
(74) Attorney, Agent, or Firm—Wenderoth, Lind & Ponack, L.L.P.

(57) ABSTRACT

The present invention provides a base for suppository comprising oily or fatty base and polyethlene.

The suppository prepared by the use of the base of the present invention has superior heat resistance which should not cause quality deterioration such as deformation and cracks, and shows good release, internal absorbability, safety and like compared to those of the suppositories used thus so far in the applied region.

8 Claims, 1 Drawing Sheet

BASE FOR SUPPOSITORY

FIELD OF THE INVENTION

The present invention relates to a base for a suppository to be applied to rectum, urethra, vagina or the like and a suppository containing that. In particular, the present invention relates to the suppository having superior heat resistance which should not cause quality deterioration such as deformation and cracks during the storage even in a relatively high temperature, and also shows the same release, internal absorbability, safety, effect and the like as those of the suppositories used thus far at the applied region, and the base therefor.

BACKGROUND OF THE INVENTION

The suppository is a solid preparation at normal temperature, and when applied to rectum, urethra, vagina or the like, is softened or melted at the body temperature, or dissolved in local mucus to make the drug absorbed into the body through the mucous membrane.

In the suppository such as a drug for treating hemorrhoids, the oily or fatty base for the suppository acts as the lubricant upon evacuation and prevent becoming more serious condition.

Many suppositories being commercially available contain oily or fatty bases such as hard fat, cacao butter and the like and their melting point is adjusted to not higher than the body temperature in order to be softened or melted at around body temperature.

For the above reasons, as to the condition for storing the suppositories, it is required to keep the suppositories in cool storage at usually not higher than 15° C. or at most 30° C., or to preserve them in the upside position of the suppository down, therefore there are many limitations in storage compared with other formulations.

It is difficult to maintain good conditions for the suppository in the case where the suppository stands at high temperature for a long time, for example, in the summer or in the car during transportation. Therefore, after the suppository has been handed to the patient, it is particularly difficult to keep it in the good condition.

On the other hand, the suppository comprising macrogol and the like has a higher melting point so as to be dissolved in the local mucus and to exhibit the effect of the drug. Therefore, it hardly causes the problems described above in the suppository comprising an oily or fatty base, however, the patient may suffer from congestion, erythema or the like on mucous membrane caused by the physical stimulation of the suppository brought about by the absorption of mucus at the local area.

The suppository containing a higher alcohol, surfactant, absorption controlling agent and the like sometimes causes poor absorption or the sustained release of the drug. Further, it may have a side effect such as strong stimulation of the local mucous membrane.

These suppositories having a high melting point may not spread by the reasons, for example, that suppository administered in the rectum is not adequately melted or softened and may not play a role of the lubricant upon evacuation which is a characteristic of the suppository. Under the circumstances, one of the objects of the present invention is to provide a suppository which does not exhibit the quality deterioration such as the deformation and crack and shows the same drug release, internal absorbability, effect and safety as those of the conventional suppositories at the applied region.

SUMMARY OF THE INVENTION

As a result of the efforts of the present inventors, it was found that a base for a suppository comprising oily or fatty base and polyethylene, if necessary further polyglycerin fatty acid ester, is capable of achieving the above objects. Namely, the present invention relates to, (1) A base for a suppository comprising oily or fatty base and polyethylene, (2) The base for the suppository according to (1) further comprising polyglycerin fatty acid ester, (3) The base for the suppository according to (1) or (2), wherein the weight ratio of the oily or fatty base or the total amount of oily or fatty base and polyglycerin fatty acid ester to polyethylene is 1:0.01–0.5, (4) The base for the suppository according to one of (1) to (3), wherein the content of polyethylene in the total weight of the base for suppository is 1 to 20 weight %, (5) The base for the suppository according to one of (1) to (4), wherein the average molecular weight of polyethylene is 500 to 30,000, (6) The base for the suppository according to (2) or (3), wherein the content of polyglycerin fatty acid ester in the total weight of the base for the suppository is 0.5 to 10 weight %, (7) The base for the suppository according to (1) or (2), wherein the oily or fatty base is at least one member selected from the group consisting cacao butter, lauric oil, beef tallow and hard fat, or the above base to which at least one member selected from the group consisting of coconut oil, palm kernel oil, tsubaki oil, olive oil, soybean oil, sesame oil, corn oil, middle chain fatty acid triglyceride, liquid petrolatum or isopropyl myristate being liquid at the normal temperature is added, (8) A suppository comprising a drug and the base for suppository according to (1) or (2), and (9) The suppository according to (8), wherein the drug is at least one member selected from the group consisting adrenocortical hormone, local anesthetic, antipyretic-analgesic-antiphlogistic, antiphlogistic-antipruritus-wound healing agent, vitamin, sulfa drug, antibiotic, fungicide, bactericide, vasoconstrictor, antihistamine, narcotic, hypnotic sedative, antianxiety drug, antiepileptic, stimulant-analeptic, antiparkinsonism drug, central nervous system acting drug, skeletal muscle relaxant, autonomic drug, spasmolytic, antivertigos, cardiotonic, antiarrythmic drug, diuretic, antihypertensive agent, coronary vasodilator, peripheral vasodilator, antihyperlipemia agent, respiratory accelerator, antidiarrheic-intestinal function controlling agent, peputic ulcer treating agent, bronchodilator, antiallergic drug, cathartic, clyster, cholagogue and various hormones except for adrenocortical hormone.

DETAILED DESCRIPTION OF THE INVENTION

The oily or fatty base used in the present invention may include cacao butter, lauric oil, beef tallow and hard fat, and the above base to which at least one member selected from the group consisting of coconut oil, palm kernel oil, tsubaki oil, olive oil, soybean oil, sesame oil, corn oil, middle chin fatty acid triglyceride, liquid petrolatum or isopropyl myristate being liquid at the normal temperature (15–25° C.) is added, preferably hard fat.

The polyethylene used in the present invention may be obtained by polymerization of ethylene, and the average molecular weight thereof may be usually about 500 to 30,000, preferably about 1,000 to 5,000.

The content of polyethylene in the total amount of the base for suppository may be 1 to 20 weight %, preferably 3 to 15 weight %.

The polyglycerin fatty acid ester used in the present invention may be obtained by polymerization of glycerin followed by esterification using fatty acid. The degree of polymerization of glycerin may be about 2 to 10, preferably about 4 to 10. The number of fatty acid may be about 1 to 10, preferably about 5 to 10. As the fatty acid, there is no particular limitation, but preferably exemplified by saturated fatty acid having 8 to 20 carbon atoms, especially, stearic acid. As the polyglycerin fatty acid ester, there may be exemplified by tetraglyceryl pentastearate, hexaglyceryl pentastearate, decaglyceryl pentastearate, decaglyceryl decastearate and the like, but not limited thereto. The content of polyglycerin fatty acid ester in the total amount of the base for the suppository may be usually 0.5 to 10 weight %, preferably 1 to 7 weight %. The weight ratio of the oily or fatty base or the mixture of oily or fatty base and polyglycerin fatty acid ester to polyethylene may be usually 1:0.01–0.5, preferably 1:0.03–0.3.

As the drug compounded in the suppository of the present invention, there may be exemplified by one or more members selected from the group consisting of adrenocortical hormone such as prednisolone acetate, prednisolone, hydrocortisone acetate, hydrocortisone, cortisone acetate, cortisone, dexamethasone acetate, dexamethasone, prednisolone valeicacetate or triamcinolone acetate, local anesthetic such as lidocaine hydrochloride, lidocaine, dibucaine hydrochloride, dibucaine, procaine hydrochloride, procaine, tetracaine hydrochloride, tetracaine, chloroprocaine hydrochloride, chloroprocaine, bupivacaine hydrochloride, bupivacaine, propalacaine hydrochloride, propalacaine, mepurylcaine hydrochloride, mepurylcaine, ethyl aminobenzoate, orsocaine, oxethazaine, p-butylaminobenzoyldiethylaminoethanol hydrochloride, oxypolyethoxydecane or scopolia extract, antipyretic analgesic antiphlogistic such as aspirin, acetaminophen, trifenamic acid, phenacetin, diclofenac sodium, indometacin, mefenamic acid, aminopyrine, ibuprofen, ethenzamide or piroxicam, antiphlogistic-antipruritus-wound healing agent such as glycyrrhetinic acid, dimethylisopropyl azulene, ichthammol, camphor, crotamiton, lysozyme chloride, tribenoside, aluminum potassium sulfate, lithospermum root extract, rosskastanien extract, witch hazel extract, processed cana brava, purified egg yolk lecithin, egg yolk oil, d-camphor, dl-camphor, mentha oil, 1-menthol, dl-menthol, eucalyptus oil, allantoin or aluminum chlorohydroxy allantoinate, vitamin such as tocopherol acetate, tocopherol, ergocalciphenol, retinol palmitate, retinol acetate, pyridoxine hydrochloride, pyridoxamine hydrochloride, pyridoxamine phosphate, pyridoxal hydrochloride, pyridoxal phosphate, riboflavin, riboflavin butyrate, vitamin A oil, higher liver oil or liver oil, sulfa drug such as sulfadiazine, sulfisomidin, sulfisomidin sodium or homosulfamine, antibiotic or fungicide such as erythromycin, tetracycline, tetracycline hydrochloride, oxytetracycline hydrochloride, streptomycin sulfate, gentamicin sulfate, fradiomycin sulfate, kanamycin sulfate, clotrimazole, miconazole, tinidazole, miconazole nitrate, oxiconazole, metronidazole, isoconazole nitrate, trichomycin, pimaricin or econazole nitrate, bactericide such as acrinol, alkyl polyaminoethylglycine, isopropyl methylphenol, cetylpyridinium chloride, dequalinium chloride, berberine chloride, benzalkonium chloride, chlorhexidine hydrochloride, chlorhexidine gluconate solution, cetrimide, phenol or resorcin, vasoconstrictor such as epinephrine hydrochloride, ephedrine hydrochloride, tetrahydrozoline hydrochloride, naphazoline hydrochloride, phenylephrine hydrochloride or dl-methylephedrine hydrochloride, antihistamine such as diphenhydramine, diphenhydramine hydrochloride, diphenhydramine tannate, diphenhydramine lauryl sulfate, chlorpheniramine maleate or diphenylpyraline hydrochloride, narcotic such as morphine hydrochloride, ethylmorphine hydrochloride, morphine sulfate, codeine phosphate, dihydrocodeine phosphate, cocaine hydrochloride or pethidine hydrochloride, but not limited thereto.

The weight percent of the drug used in the suppository may be about 0.1 to 10 weight %, but not limited thereto.

If desired, a suitable amount of absorption controlling agent, surfactant, dissolution coadjuvant, water, stabilizer, preservative, excipient and the like may be further added in the suppository of the present invention.

The suppository may be produced by known methods per se, for example, a method comprising a step of melting the base for the suppository, a step of producing uniform dispersion or dissolution of the drug and other components in need therein, a step of filling it in the mold for the suppository and a step of hardening it at room temperature (15–25° C.) or below.

Also, the drug may be dispersed or dissolved in the previously melted base, cooled to about 35° C., and thereto is added a mixture prepared by melting polyethylene powder in a part of the base by heating. Then, the resulting mixture may be kept at the temperature ranging from 60 to 90°, filled in the mold for the suppository and hardened at about room temperature (15–25° C.) or below.

EXAMPLE

The present invention is concretely explained by the following Examples, Comparative Examples and Test Examples.

Example 1

| | |
|---|---|
| Polyethylene (average molecular weight 5,000) | 87.5 mg |
| Hard Fat | q.s. |
| Total amount | 1750 mg |

Polyethylene was uniformly mixed with hard fat previously melted at 60°. The mixture was heated to 130° C. in the oil bath to melt the polyethylene, filled in the aluminum mold and cooled at room temperature (25° C.) to obtain the suppository.

Example 2

| | |
|---|---|
| Polyethylene (average molecular weight 1,500) | 175 mg |
| Hard Fat | q.s. |
| Total Amount | 1750 mg |

Polyethylene was uniformly mixed with hard fat previously melted at 60° C. The mixture was heated to 130° C. in the oil bath to melt the polyethylene, filled in the aluminum mold and cooled at room temperature (25° C.) to obtain the suppository.

Example 3

| | |
|---|---:|
| Prednisolone Acetate | 1 mg |
| Polyethylene (average molecular weight 5,000) | 87.5 mg |
| Hard Fat | q.s. |
| Total Amount | 1750 mg |

Prednisolone acetate and polyethylene were uniformly mixed with hard fat previously melted at 60° C. The mixture was heated to 130° C. in the oil bath to melt the polyethylene, filled in the aluminum mold and cooled at room temperature (25° C.) to obtain the suppository.

Example 4

| | |
|---|---:|
| Prednisolone Acetate | 1 mg |
| Polyethylene (average molecular weight 1,500) | 175 mg |
| Hard Fat | q.s. |
| Total Amount | 1750 mg |

Prednisolone acetate and polyethylene were uniformly mixed with hard fat previously melted at 60° C. The mixture was heated to 130w in the oil bath to melt the polyethylene, filled in the aluminum mold and cooled at room temperature (25° C.) to obtain the suppository.

Example 5

| | |
|---|---:|
| Lidocaine | 60 mg |
| Prednisolone Acetate | 1 mg |
| Tocopherol Acetate | 60 mg |
| Crotamiton | 100 mg |
| Chlorhexidine Hydrochloride | 10 mg |
| Polyethylene (average molecular weight 5,000) | 87.5 mg |
| Hard Fat | q.s. |
| Total Amount | 1750 mg |

Lidocaine and tocopherol acetate were mixed with hard fat previously melted at 60° C. Prednisolone acetate dissolved in crotamiton was added to the above mixture. Further chlorhexidine hydrochloride and polyethylene were uniformly mixed into the above mixture and heated to 130° C. in the oil bath to melt the polyethylene, filled in the aluminum mold and cooled at room temperature (25° C.) to obtain the suppository.

Example 6

| | |
|---|---:|
| Lidocaine | 40 mg |
| Tribenoside | 200 mg |
| Polyethylene (average molecular weight 5,000) | 87.5 mg |
| Hard Fat | q.s. |
| Total Amount | 1750 mg |

Lidocaine and tribenoside were melted into hard fat previously melted at 60° C. Polyethylene was uniformly mixed with the above mixture and heated to 130° C. in the oil bath to melt the polyethylene. The mixture was filled in the aluminum mold and cooled at room temperature (25° C.) to obtain the suppository.

Example 7

| | |
|---|---:|
| Acetaminophen | 200 mg |
| Polyethylene (average molecular weight 5,000) | 87.5 mg |
| Hard Fat | q.s. |
| Total Amount | 1750 mg |

Acetaminophen and polyethylene were mixed with hard fat previously melted at 60° C. The mixture was heated to 130° C. in the oil bath to melt the polyethylene, filled in the aluminum mold and cooled at room temperature (25° C.) to obtain the suppository.

Example 8

| | |
|---|---:|
| Lidocaine | 60 mg |
| Prednisolone Acetate | 1 mg |
| Tocopherol Acetate | 60 mg |
| Allantoin | 20 mg |
| Diphenhydramine Hydrochloride | 20 mg |
| dl-Camphor | 20 mg |
| Decaglyceryl Decastearate | 17.5 mg |
| Polyethylene (average molecular weight 3,500) | 140 mg |
| Hard Fat | q.s. |
| Total Amount | 1750 mg |

Lidocaine, tocopherol acetate and decaglyceryl decastearate were mixed with a part of hard fat previously melted at 60° C. and cooled to about 35° C. dl-Camphor was added into the above mixture and dissolved. Further, prednisolone acetate, allantoin and diphenhydramine hydrochloride were dispersed in a part of melted hard fat and cooled to about 35° C. to mix with the above mixture. Separately, polyethylene was added into a part of melted hard fat, mixed uniformly and melted by heating at 110° C. in oil the bath to mix with the above mixture. The mixture was adjusted to about 80° C., filled in the aluminum mold and cooled at room temperature (25° C.) to obtain the suppository.

Example 9

| | |
|---|---:|
| Lidocaine | 60 mg |
| Prednisolone Acetate | 1 mg |
| Tocopherol Acetate | 60 mg |
| Allantoin | 20 mg |
| Polyethylene (average molecular weight 3,500) | 140 mg |
| Hard Fat | q.s. |
| Total Amount | 1750 mg |

Lidocaine and tocopherol acetate were mixed with a part of hard fat previously melted at 60° C. and cooled to about 35° C. Further, prednisolone acetate and allantoin were dispersed in a part of melted hard fat and cooled to about 35° C. to mix with the above mixture. Separately, polyethylene was mixed uniformly with a part of melted hard fat. The mixture was heated to 110° C. in the oil the bath to melt the polyethylene and mixed with the above mixture. The resultant mixture was adjusted to about 80° C., filled in the aluminum mold and cooled at room temperature (25° C.) to obtain the suppository.

Example 10

| Lidocaine | 60 mg |
| --- | --- |
| Prednisolone Acetate | 1 mg |
| Tocopherol Acetate | 60 mg |
| Allantoin | 20 mg |
| Tetraglyceryl Pentastearate | 87.5 mg |
| Polyethylene (average molecular weight 3,500) | 140 mg |
| Hard Fat | q.s. |
| Total Amount | 1750 mg |

Lidocaine, tocopherol acetate and tetraglyceryl pentastearate were mixed with a part of hard fat previously melted at 60° C. and cooled to about 35° C. Further, prednisolone acetate and allantoin were dispersed into a part of melted hard fat and cooled to about 35° C. to mix with the above mixture. Separately, polyethylene was mixed uniformly with a part of hard fat previously melted at 60° C. and melted by herating at 110° C. in oil the bath to mixt with the above mixture. The resultant mixture was adjusted to about 80° C. filled in the aluminum mold and cooled at room temperature (25° C.) to obtain the suppository.

Example 11

| Lidocaine | 60 mg |
| --- | --- |
| Prednisolone Acetate | 1 mg |
| Tocopherol Acetate | 60 mg |
| Allantoin | 20 mg |
| Decaglyceryl Decastearate | 17.5 mg |
| Polyethylene (average molecular weight 3,500) | 140 mg |
| Hard Fat | q.s. |
| Total Amount | 1750 mg |

Lidocaine, tocopherol acetate and decaglyceryl decastearate were mixed with a part of hard fat previously melted at 60° C. and cooled to about 35° C. Further, prednisolone acetate and allantoin were dispersed into a part of melted hard fat and cooled to about 35° C. to mix with the above mixture. Separately, polyethylene was added into a part of melted hard fat, mixed uniformly and melted by heating at 110° C. in the oil bath to mix with the above mixture. The mixture was adjusted to about 80° C., filled in the aluminum mold and cooled at room temperature (25° C.) to obtain the suppository.

COMPARATIVE EXAMPLE 1

Hard fat melted at 60° C. was filled in the aluminum mold and cooled at room temperature (25° C.) to obtain the suppository.

Comparative Example 2

| Prednisolone Acetate | 1 mg |
| --- | --- |
| Hard Fat | q.s. |
| Total Amount | 1750 mg |

Prednisolone acetate was uniformly mixed with hard fat previously melted at 60° C. The mixture was filled in the aluminum mold and cooled at room temperature (25° C.) to obtain the suppository.

TEST EXAMPLE 1

The suppositories obtained in Examples 1 to 11 and Comparative Examples 1 and 2 were stored at each temperature of 40° C., 50° C. and 60° C. in the laid position for a predetermined period, and then cooled to the room temperature (25° C.). From the appearance of the suppositories, the occurrence of the deformation, crack and the like thereof were observed. The results were shown in Table 1.

TABLE 1

Storage Condition and Occurrence of Deformation and Crack (n = 10)

| | Initial (Room temperature) | 40° C. for 1 day | 50° C. for 1 hour | 60° C. for 1 hour |
| --- | --- | --- | --- | --- |
| Example 1 | 0 | 0 | 0 | 0 |
| Example 2 | 0 | 0 | 0 | 0 |
| Example 3 | 0 | 0 | 0 | 0 |
| Example 4 | 0 | 0 | 0 | 0 |
| Example 5 | 0 | 0 | 0 | 0 |
| Example 6 | 0 | 0 | 0 | 0 |
| Example 7 | 0 | 0 | 0 | 0 |
| Example 8 | 0 | 0 | 0 | 0 |
| Example 9 | 0 | 0 | 0 | 0 |
| Example 10 | 0 | 0 | 0 | 0 |
| Example 11 | 0 | 0 | 0 | 0 |
| Comparative Example 1 | 0 | 10 | 10 | 10 |
| Comparative Example 2 | 0 | 10 | 10 | 10 |

As shown in Table 1, all the suppositories of Comparative Examples 1 and 2 had the occurrence of the deformation and cracks, but the suppositories of Examples 1 to 11, which are the products of the present invention, had no occurrence of the deformation or cracks.

From the results described above, it is clear that the suppository of the present invention are far more superior to those containing no polyethylene of Comparative Examples 1 and 2, in the occurrence of the deformation and cracks.

TEST EXAMPLE 2

The appearance of the suppositories obtained in Examples 9, 10 and 11 was observed, and the occurrence of the chaps on the surface of the suppository and on the cross section thereof when the suppository was divided transversely by half were detected. The results were shown in Table 2.

Each suppositories obtained in the above Examples had no deformation nor crack. Herein the chap is a minute crack which should not affect the utility and effect of the suppository.

TABLE 2

Number of Suppository having Chaps (n = 100)

| | Polyglycerin fatty acid ester | On the surface of the suppository | On the cross section of the suppository |
| --- | --- | --- | --- |
| Example 9 | — | 3 | 22 |
| Example 10 | 5% | 0 | 2 |
| Example 11 | 1% | 0 | 0 |

As shown in Table 2, the suppository of Example 9 containing no polyglycerin fatty acid ester had the chaps on the surface thereof and in the central part of the section thereof, but the suppositories of Example 10 and 11 containing the polyglycerin fatty acid ester had no chap on the surface thereof and had only minute chaps in the central part of the section thereof.

From the results described above, it is clear that the compounding polyglycerin fatty acid ester in the suppository base is effective in inhibiting the occurrence of the chaps on the surface and inside of the suppository.

TEST EXAMPLE 3

Test for Antiphlogistic Action

A cotton bud immersed in prophlogistic (distilled water:pyridine:ether:solution of 6% croton oil in ether =1:4:5:10) was inserted in rectum of a male rat not fed for 24 hours to occur the inflammation. After the occurrence of the inflammation, the rat was instantly administered 150 mg of each sample obtained in Examples 3 and 4 and Comparative Example 2 and closed the anal region by using the suture.

The rat was shed brood at the time of 24 hours after the occurrence of the inflammation. Then, 15 mm of the rectal-anal region was cut out and measured the wet weight. The recto-anus-coefficient (RAC) which is an index of the degree of edema was calculated in accordance with the following equation (a). Further, the inhibition rate of the edema was calculated in accordance with the following equation (b) by using RAC and used as an index of the antiphlogistic action.

$$RAC = \frac{\text{Wet weight of anarectal region (g)} \times 100}{\text{Body weight (g)}} \quad (a)$$

Ratio of inhibition of edema (%) = (b)

$$\left\{1 - \frac{RAC \text{ of sample administered group} - RAC \text{ of non-treated group}}{RAC \text{ of control group} - RAC \text{ of non-treated group}}\right\} \times 100$$

The non treated group was not administered the prophlogistic and the sample. The control group was administered the prophlogistic, but not administered the sample. The results are shown in Table 3.

TABLE 3

(Average ± Standard error)

| | Number of n | RAC | Ratio of inhibition of the edema (%) |
|---|---|---|---|
| Not treated group | 10 | 0.917 ± 0.027 | — |
| Control group | 10 | 3.319 ± 0.120 | — |
| Example 3 | 8 | 2.448 ± 0.085 | 37.18 ± 2.94 |
| Example 4 | 5 | 2.253 ± 0.190 | 41.54 ± 9.80 |
| Comparative Example 2 | 10 | 2.494 ± 0.164 | 34.34 ± 6.83 |

From the results described above, it was confirmed that the suppositories of Examples 3 and 4 showed the same antiphlogistic effect as that of the suppository of Comparative Example 2, in aspect of the effect of the drug.

TEST EXAMPLE 4

Test for Concentration of Prednisolone Acetate in Plasma of a Rat 300 mg of each sample obtained in Examples 3 and 4 and Comparative Example 2 was administered to the rectum of male rat not fed for 24 hours. A determined amount of blood was collected from the caudal vein at the time of 0.25, 0.5, 1 and 3 hours after the administration. And at the time of 6 hours after the administration, the whole brood was collected. Then prednisolone was extracted from plasma and the concentration of prednisolone was measured by column-switching method of high performance liquid chromatography. The amount of prednisolone was calculated by using the calibration curve previously prepared.

The results are shown in Table 4 and FIG. 1. The conditions of the high performance liquid chromatography:

Column (1): a column filled with octadecylsilyl silica gel for the liquid chromatography (average diameter of the particle: about 3 μm, length: about 75 mm, inner diameter: about 4.6 mm)

Column (2): a column filled with octadecylsiyl silica gel for the liquid chromatography (average diameter of the particle: about 5 μm, length: about 150 mm, inner diameter: about 4.6mm)

Mobile phase (1): 0.025M potassium dihydrogen phosphate buffer (pH 7. 0)/acetonitrile (3:1)

Mobile phase (2): 0.025M potassium dihydrogen phosphate buffer (pH 7.0)/acetonitrile (2:1)

Detector: UV absorption on photometer (measurement wavelength: 245 nm)

Temperature of the column: a constant temperature of about 40° C.

Applied amount: 100 μl

As shown in [Table 4]and [FIG 1], it was confirmed that the suppositories obtained in Examples 3 and 4 had almost the same max. concentration in plasma (Cmax) and the area under the curve of the concentration in plasma and time (AUC) as those of the suppository obtained in Comparative Example 2 at the time of 60 minutes after the administration.

TABLE 4

Pharmacokinetic parameter (n = 6 Average ± Standard deviation )

| | Tmax (min) | Cmax (ng/ml) | $AUC_{0-6 h}$ |
|---|---|---|---|
| Example 3 | 60 | 15.3 ± 3.6 | 43.2 ± 11.6 |
| Example 4 | 60 | 18.6 ± 5.5 | 52.9 ± 13.2 |
| Comparative Example 2 | 60 | 17.0 ± 3.6 | 49.5 ± 13.8 |

The conventional suppositories using oily or fatty base have the occurrence of the deformation and crack on a storage at over 30° C. But the present suppository prepared by the use of the base comprising the oily or fatty base and polyethylene, in need, further also polyglycerin fatty acid ester, has no deformation nor crack on storage at comparatively high temperature and hardly has even chops which do not influence on the use.

Also, the suppository of the present invention is in no way inferior to the conventional suppositories in drug release, internal absorbability, safety, feeling for use and the like.

While a detailed description of the invention has been provided above, the invention may be embodied in other specific forms without departing form the spirit thereof. The disclosed embodiments should be considered as illustrative rather than restrictive, the scope of the invention being indicated by the appended claims, with all changes that come within the meaning and range of equivalency of the claims being intended to be embraced therein.

Figure 1:
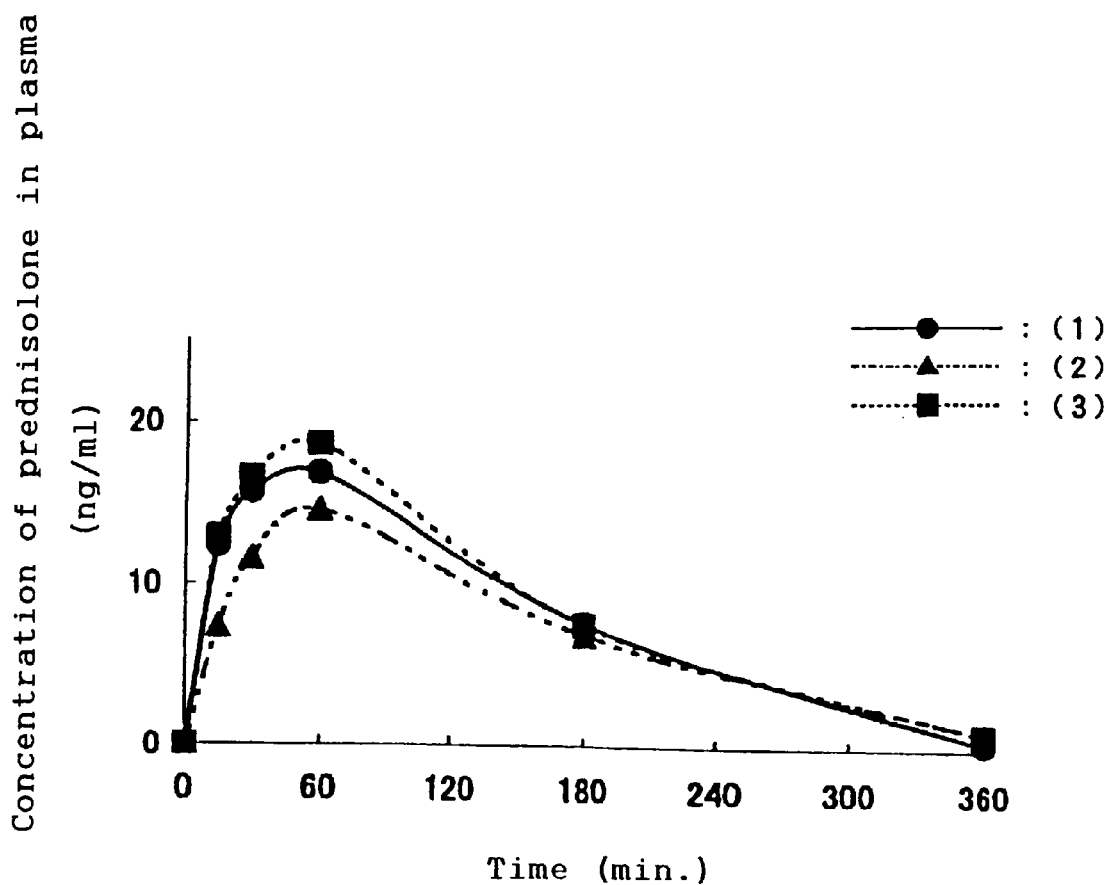
FIG. 1 The results of the measurement of the concentration of prednisolone in plasma.

Explanation of symbols (1): The suppository of Comparative Example 2

(2): The suppository of Example 3

(3): The suppository of Example 4

We claim:

1. A base for a suppository comprising (a) oily or fatty base, (b) polyethylene and (c) polyglycerin fatty acid ester.

2. The base for the suppository according to claim 1, wherein the weight ratio of the oily or fatty base or the total amount of oily or fatty base and polyglycerin fatty acid ester to polyethylene is 1:0.01–0.5.

3. The base for the suppository according to claim 1, wherein the content of polyethylene in the total weight of the base for suppository is 1 to 20 weight %.

4. The base for the suppository according to claim 1, wherein the average molecular weight of polyethylene is 500 to 30,000.

5. The base for the suppository according to claim 1, wherein the content of polyglycerin fatty acid ester in the total weight of the base for the suppository is 0.5 to 10 weight %.

6. The base for the suppository according to claim 1, wherein the oily or fatty base is at least one member selected from the group consisting of cacao butter, lauric oil, beef tallow and hard fat, or the above base to which at least one member selected from the group consisting of coconut oil, palm kernel oil, tsubaki oil, olive oil, soybean oil, sesame oil, corn oil, middle chain fatty acid triglyceride, liquid petrolatum and isopropyl myristate being liquid at the normal temperature is added.

7. A suppository comprising a drug and the base for suppository according to claim 1.

8. The suppository according to claim 7, wherein the drug is at least one member selected from the group consisting of adrenocortical hormone, local anesthetic, antipyretic-analgesic-antiphlogistic, antiphlogistic-antipruritus-wound healing agent, vitamin, sulfa drug, antibiotic, fingicide, bactericide, vasoconstrictor, antihistamine, narcotic, hypnotic sedative, antianxiety drug, antiepileptic, stimulant-analeptic, antiparkinsonism drug, central nervous system acting drug, skeletal muscle relaxant, autonomic drug, spasmolytic, antivertigos, cardiotonic, antiarrythinic drug, diuretic, antihypertensive agent, coronary vasodilator, peripheral vasodilator, antihyperlipemia agent, respiratory accelerator, antidiarrheic-intestinal function controlling agent, peputic ulcer treating agent, bronchodilator, antiallergic drug, cathartic, clyster, cholagogue and hormones except for adrenocortical hormone.

* * * * *